United States Patent [19]

Lai

[11] Patent Number: 5,756,540
[45] Date of Patent: May 26, 1998

[54] METHODS FOR IN VIVO REDUCTION OF NITRIC OXIDE LEVELS AND COMPOSITIONS USEFUL THEREFOR

[75] Inventor: Ching-San Lai, Brookfield, Wis.

[73] Assignee: MCW Research Foundation, Inc., Milwaukee, Wis.

[21] Appl. No.: 459,518

[22] Filed: Jun. 2, 1995

[51] Int. Cl.$^6$ .......................... A61K 31/28; C07F 13/00; C07F 15/06
[52] U.S. Cl. .................. 514/492; 514/499; 514/501; 514/502; 556/50; 556/134; 556/148; 562/27
[58] Field of Search .......................... 556/40, 134, 148; 562/27; 514/492, 499, 501, 502

[56] References Cited

U.S. PATENT DOCUMENTS

| | | | |
|---|---|---|---|
| 1,863,572 | 6/1932 | Lommel et al. | 556/50 |
| 2,876,159 | 3/1959 | Sunderman et al. | 167/65 |
| 4,160,452 | 7/1979 | Theeuwes | 128/260 |
| 4,256,108 | 3/1981 | Theeuwes | 128/260 |
| 4,265,874 | 5/1981 | Bonsen et al. | 424/15 |
| 4,554,108 | 11/1985 | Kimble et al. | 260/455 A |
| 4,595,538 | 6/1986 | Kimble et al. | 260/502.56 |
| 5,358,703 | 10/1994 | Lai | 424/9 |

FOREIGN PATENT DOCUMENTS 0901094  7/1962  United Kingdom.

OTHER PUBLICATIONS

Aisaka et al., "N$_G$–Methylarginine, an Inhibitor of Endothelium–Derived Nitric Oxide Synthesis, is a Potent Pressor Agent in the Guinea Pig: Does Nitric Oxide Regulate Blood Pressure in vivo?" *Biochem. Biophys. Res. Commun.* 160:881–886 (1989).

Aisaka et al. "L–Arginine Availability Determines the Duration of Acetylcholine–Induced Systematic Vasodilation in vivo" *Biomedical and Biophysical Research Communications* 163:710–717 (1989).

Akaike et al., "Therapeutic Effects of Imidazolineoxyl N–Oxide Against Endotoxin Shock Through its Direct Nitric Oxide–Scavenging Activity" *Biochemical and Biophysical Research Communications* 202:923–930 (1994).

Alving et al., "Increased Amount of Nitric Oxide in Exhaled Air of Asthmatics" *Eur. Respir. J.* 6:1368–1370 (1993).

Balter, Michael. "Cytokines Mive From the Margins Into the Spotlight" *Science* 268:205–206 (1995).

Barnes and Liew, "Nitric Oxide and Asthmatic Inflammation" *Immunology Today* 16:128–130 (1995).

Bartholomew, B., "A Rapid Method for the Assay of Nitrate in Urine Using the Nitrate Reductase Enzyme of *Escherichia Coli*" *Food Chem. Toxic.* 22:541–543 (1984).

Boughton–Smith et al., "Nitric Oxide Synthase Activity in Ulcerative colitis and Crohn's Disease" *Lancet* 342:338–340 (1993).

Bukrinsky et al., "Regulation of Nitric Oside Synthase Activity in Human Immunodeficiency Virus Type 1 (HIV–1) Infected Monocytes: Implications for HIV–Associated Neurological Disease" *J. Exp. Med.* 181:735–745 (1995).

Cattell et al., "Localization of Inducible Nitric Oxide Synthase in Acute Renal Allograft Rejection in the Rat" *Transplantation* 58:1399–1402 (1994).

Clària et al., "Pathogenisis of Arterial Hypotension in Cirrhotic Rats with Ascites: Role of Endogenous Nitric Oxide" *Hepatology* 15:343–349 (1992).

Corbett et al., "Nitric Oxide Mediates Cytokine–Induced Inhibition of Insulin Secretion by Human Islets of Langerhans" *Proc. Natl. Acad. Sci.* 90:1731–1735 (1993).

Devlin et al., "Nitric Oxide Generation" *Transplantation* 58:592–595 (1994).

Dorheim et al., "Niotric Oxide Synthase Acitivity is Elevated in Brain Microvessels in Alzheimer's Disease" *Biochemical and Biophysical Research Communications* 205:659–665 (1994).

Eizirik et al., "Cytokines Suppress Human Islet Function Irrespective of Their Effects on Nitric Oxide Generation" *J. Clin. Invest.* 93:1968–1974 (1994).

Eizirik et al., "Major Species Differences Between Humans and Rodents in the Susceptibility to Pancreatic β–Cell Injury" *Proc. Natl. Acad. Sci.* 91:9253–9256 (1994).

Evans et al., "Evidence of Increased Nitiric Oxide Production in Patients with the Sepsis Syndrome" *Circulatory Shock* 41:77–81 (1993).

Evans et al., "Inhibition of Nitroc Oxide Synthase in Experimental Gram–Negative Sepsis" *Journal of Infectious Diseases* 169:343–349 (1994).

(List continued on next page.)

*Primary Examiner*—Porfirio Nazario-Gonzalez
*Attorney, Agent, or Firm*—Pretty, Schroeder, Brueggemann & Clark; Stephen E. Reiter

[57] ABSTRACT

In accordance with the present invention, there are provided methods for the in vivo reduction of nitric oxide levels in a mammalian subject. In contrast to the inhibitory approach described in the prior art (i.e., wherein the function of the enzymes responsible for nitric oxide production is inhibited), the present invention employs a scavenging approach whereby overproduced nitric oxide is bound in vivo to a suitable nitric oxide scavenger. The resulting complex renders the nitric oxide harmless, and is eventually excreted in the urine of the host. Further in accordance with the present invention, there are provided compositions and formulations useful for carrying out the above-described methods. An exemplary nitric oxide scavenger contemplated for use in the practice of the present invention is a dithiocarbamate-ferrous iron complex. The present invention relates to methods for reducing in vivo levels of ·NO as a means of treating subjects afflicted with inflammatory and/or infectious disease. Dithiocarbamate-containing nitric oxide scavengers are administered to a host in need of such treatment; these scavengers interact with in vivo produced ·NO, forming a stable dithiocarbamate-metal-NO complex. The NO-containing complex is then filtered through the kidneys, concentrated in the urine, and eventually excreted by the subject, thereby reducing in vivo ·NO levels.

39 Claims, 6 Drawing Sheets

OTHER PUBLICATIONS

Farrel et al., "Increased Concentrations of Nitrite in Synovial Fluid and Serum Samples Suggest Increased Nitric Oxide Synthesis in Rheumatic Diseases" *Annals of Rhumatic Diseases* 51:1219–1222 (1992).

Froncisz and Hyde, "The Loop–Gap Resonator: A New Microwave Lumped Circut ESR Sample Structure" *J. Magn. Reson.* 47:515–521 (1982).

Gómez–Jiménez et al., "L–Agrinine: Nitric Oxide Pathway in Endotoxemia and Human Septic Shock" *Critical Care Medicine* 23:253–258 (1995).

Green et al., "Analysis of Nitrate, Nitrite, and $[_{15}N]$Nitrate in Biological Fluids" *Anal. Biochem.* 126:131–138 (1982).

Guarner et al., "Increased Serum Nitrite and Nitrate Levels in Patients with Cirrhosis: Relationship to Endotoxemaia" *Heptology* 18:1139–1143 (1993).

Hamid et al. "Induction of Nitric Oxide Synthase in Asthma" *Lancet* 342:1510–1513 (1993).

Harbrecht et al., "Inhibition of Nitric Oxide Synthesis During Endotoxemia Promotes Intrahepatic Thrombosis and an Oxygen Radical–Mediated Hepatic Injury" *J. Leuk. Biol.* 52:390–394 (1992).

Henderson et al., "The Effects of Nitric Oxide Ingibition on Regional Hemodynamics During Hyperdynamic Endotoxemia" *Arch. Surg.* 129:1271–1275 (1994).

Hibbs et al., "Evidence for Cytokine–Inducible Nitric Oxide Synthesis from L–Argininge in Patients Receiving Interleukin–2 Therapy" *J. Clin. Invest.* 89:867–877 (1992).

Hotchkiss et al., "Inhibition of NO Synthesis in Septic Shock" *Lancet* 339:434–435 (1992).

Ignarro, L.J., "Biosynthesis and Metabolism of Enbothelium–Derived Nitric Oxide" *Ann. Rev. Toxicol* 30:535–560 (1990).

Johnson et al., "Evidence for Increased Nitric Oxide Production in Multiple Sclerosis" *Journal of Neurology, Neurosurgery and Phyciatry* 58:107 (1995).

Kaur and Halliwell, "Evidence for NitricOxide Mediated Oxidative Damage in Chromic Inflammation" *FEBS Letters* 350:9–12 (1994).

Kelm and Schrader, "Control of Coronary Vascular Control by Nitric Oxide" *Circ. Res.* 66:1561–1575 (1990).

Kharitonov et al., "Increased Nitric Oxide in Exhaled Air of Asthmatic Patients" *Lancet* 343:133–135 (1994).

Kilbourn et al., "$N_G$–Methyl–L–Arginine Inhibits Tumor Necrosis Factor–Induced Hypotension: Implications for the Involvement of Nitric Oxide" *Proc. Natl. Adac. Sci.* 87:3629–3632 (1990).

Kilbourn et al., "Reversal of Endotoxin–Mediated Shock by $N_G$–Methyl–L–Arginine, an Inhibitor of Nitric Oxide Synthesis" *Biochemical and Biophysical Research Communications* 172:1132–1138 (1990).

Kilbourn and Griffith, "Overproduction of Nitric Oxide in Cytokine–Mediated and Septic Shock" *J. Natl. Cancer Instit.* 84:827–831 (1992).

Kilbourn et al., "Cell–Free Hemoglobin Reverses the Endotoxin–Mediated Hyporesponsivity of Rat Aortic Rings to α–Adrenergic Agents" *Biochemical and Biophysical Research Communications* 199:155–162 (1994).

Kilbourn et al., "$N_G$–Methyl–L–Arginine, an Inhibitor of Nitric Oxide Formation, Reverses IL–2–Mediated Hypotension in Dogs" *Journal of Applied Physiology* 76:1130–1137 (1994).

Komarov et al., "In Vivo Spin Trapping of Nitric Oxide in Mice" *Biochem. Biophys. Res. Commun.* 195:1191–1198 (1993).

Komarov and Lai, "Detection of Nitric Oxide Production in Mice by Spin–Trapping Electron Paramagnetic Resonance Spectroscopy" *Biochimica et Biophysica Acta* 1272:29–36 (1995).

Konturek et al., "Inhibition of Nitric Oxide Synthase Delays Healing of Chronic Gastric Ulcers" *European Journal of Pharmacology* 239:215–217 (1993).

Kovacs et al., "Increases in CD4 T Lymphocytes with Intermittent Courses of Interleukin–2 in Patients with Human Immunodeficiency Virus Infection" *New England Journal of Medicine* 332:567–575 (1995).

Lai and Komarov, "Spin Trapping of Nitric Oxide Produced in vivo in Septic–Shock Mice" *FEBS Lett.* 345:120–124 (1994).

Lowenstein and Synder, "Nitric Oxide, A Novel Biologic Messenger" *Cell* 70:705–707 (1992).

Lundberg et al., "Greatly Ubcreased Luminal Nitric Oxide in Ulcerative Colitis" *Lancet* 344:1673–1674 (1994).

Luss et al., "Inhibition of Nitric Oxide Synthesis Enhances the Expression of Inducible Nitric Oxide Synthase mRNA and Protein in a Modeol of Chronic Liver Inflammation" *Biochem. and Biophys. Res. Comm.* 204:635–640 (1994).

Middleton et al., "Increased Nitric Oxide Synthesis in Ulcerative Colitis" *Lancet* 341:465–466 (1993).

Miles et al., "Asssociation Between Biosynthesis of Nitric Oxide and Changes in Immunological and Vascular Parameters in Patients Treated with Interleukin–2" *European Journal of Clinical Investigation* 24:287–290 (1994).

Minnard et al., "Inhibition of Nitric Oxide Synthesis is Detrimental During Endotoxemia" *Arch. Surg.* 129:142–148 (1994).

Moncada, S., "The L–Arginie:Nitric Oxide Pathway" *Acta. Physiol. Scand.* 145:201–227 (1992).

Moncada and Higgs, "The 1991 Ulf von Euler Lecture: The L–Arginine:Nitric Oxide Pathway" *N. Eng. J. Med.* 329:2002–2012 (1993).

Nava et al., "The Role of Nitric Oxide in Endotoxic Shock: Effects of $N_G$–Monomethyl–L–Arginine" *J. Cardiovasc. Pharmacol.* 20(Suppl. 12):S132–134 (1992).

Ochoa et al., "Nitrogen Oxide Levels in Patients After Trauma and During Sepsis" *Ann. Surg.* 214:621–626 (1991).

Ogle and Qiu, "Nitric Oxide Inhibition Intensifies Cold––Restraint Induced Gastric Ulcers in Rats" *Experientia* 49:304–307 (1993).

Palmer, Richard M. J., "The discovery of Nitric Oxide in the Vessle Wall" *Arch. Surg.* 128:396–401 (1993).

Palmer et al., "Nitric Oxide Release Accounts for the Biological Activity of Endothelium–Derived Relasing Factor" *Nature* 327:524–26 (1987).

Petros et al., "Effect of Nitric Oxide Synthase Inhibitors on Hypotension in Patients with Septic Shock" *Lancet* 338:1557–1558 (1991).

Petros et al., "Effects of a Nitric Oxide Synthase Inhibitor in Humans with Septic Shock" *Cardiovascular Research* 28:34–39 (1994).

Qazi et al., "Phase I Clinical and Pharmacokinetic Study of Diethyldithiocarbamate as a Chemoprotector from Toxic Effects of Cisplatin" *Journal of the Ntional Cancer Institute* 80:1486–1488 (1988).

Rachmilewitz et al., "Enhanced Gastric Nitric Oxide Synthase Activity in Duodenal Ulcer Patients" *Gut* 35:1394–1397 (1994).

Rees et al., "Role of Endothelium–Derived Nitric Oxide in the Regulation of Blood Pressure" *Proc. Natl. Acad. Sci. USA* 86:3375–3379 (1989).

Rees et al., "Dexamethasone Prevents the Induction by Endotoxin of a Nitric Oxide Synthase and the Associated Effects on Vascular Tone an Insight into Endotoxin Shock" *Biochem. Biophys. Res. Comm.* 173:541–547 (1990).

Robertson et al., "Detrimental Hemodynamic Effects of Nitric Oxide Synthase Inhibition in Septic Shock" *Arch. Surg.* 129:149–156 (1994).

Schilling et al., "A New Approach in the Treatment of Hypotension in Human Septic Shock by $N_G$–Monomethyl–L–Arginine, an Inhibito of the Nitric Oxide Synthetase" *Intensive Care Medicine* 19:227–231 (1993).

Shinobu et al., "Sodium N–Methyl–D–glucamine Dithiocarbamate and Cadmiun Intoxication" *Acta Pharmacol. et Toxicol.* 54:189–194 (1984).

St. John and Dorinsky, "Immunologic Therapy for ARDS, Septic Shock, and Multiple Organ Failure" *Chest.* 103:932–943 (1993).

Statman et al., "Nitric OxideInhibition in the Treatment of the Sepsis Syndrome is Detrimental to Tissue Oxygenation" *J. Surg. Res.* 57:93–98 (1994).

Stefanovic–Racic et al., "Nitric Oxide and Arthritis" *ARthrities and Rhumastism* 36:1036–1044 (1993).

Stefanovic–Racic et al., "N–Monomethyl Arginine, an Inhibitor of Nitric Oxide Synthase, Suppresses the Development of Adjuvant Arthritis in Rats" *Arhtritids & Rhumatism* 37:1062–1069 (1994).

Vallance and Moncada, "Hyperdynamic Circulation in Cirrhosis: a Role for Nitric Oxide?" *Lancet* 337:776–778 (1991).

Vallance and Moncada, "Nitric Oxide: From Mediator to Medicines" *Journal of the Royal College of Physicians of London* 28:209–219 (1994).

Vicaut et al., "Nitric Oxide–Independent Response to Acetylcholine by Terminal Arterioles in Rat Cremaster Muscle" *J. Appl. Physiol.* 77:536–533 (1994).

Whittle et al., "Modulation of the Vasodepressor Actions of Acetylcholine, Bradykinin, Substance P and Endothelin in the Rat by a Specific Inhibitor of Nitric Oxide Formation" *Br. J. Pharmacol.* 98:646–652 (1989).

Winlaw et al., "Urinary Nitrate Excretion is a Noninvasive Indicator of Acute Cardiac Allograft Rejection and Nitric Oxide Production in the Rat" *Transplantation* 58:1031–1036 (1994).

Worrall et al., "Modulation if in vivo Alloreactivity by Inhibition of Inducible Nitric Oxide Synthase" *J. Exp. Med.* 181:63–70 (1995).

Yang et al., "Induction of Myocardial Nitric Oxide Synthase by Cardiac Allograft Rejection" *J. Clin. Invest.* 94:714–721 (1994).

Zweier et al., "Direct Measurement of Nitric Oxide Generation in theIschemic Heart Using Electron Paramagnetic Resonance Spectorscopy" *Journal of Biological Chemistry* 270:304–307 (1995).

10 G

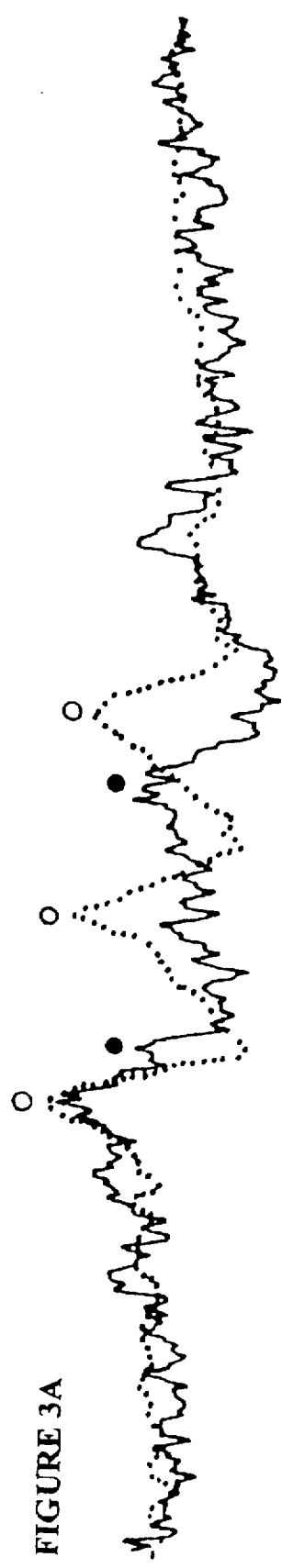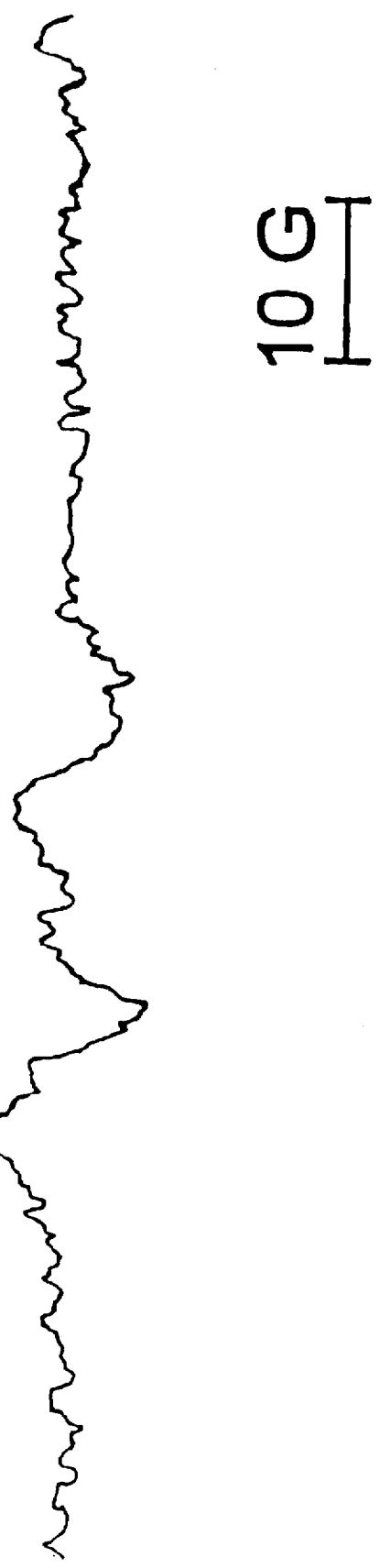
FIGURE 3A
FIGURE 3B
10 G

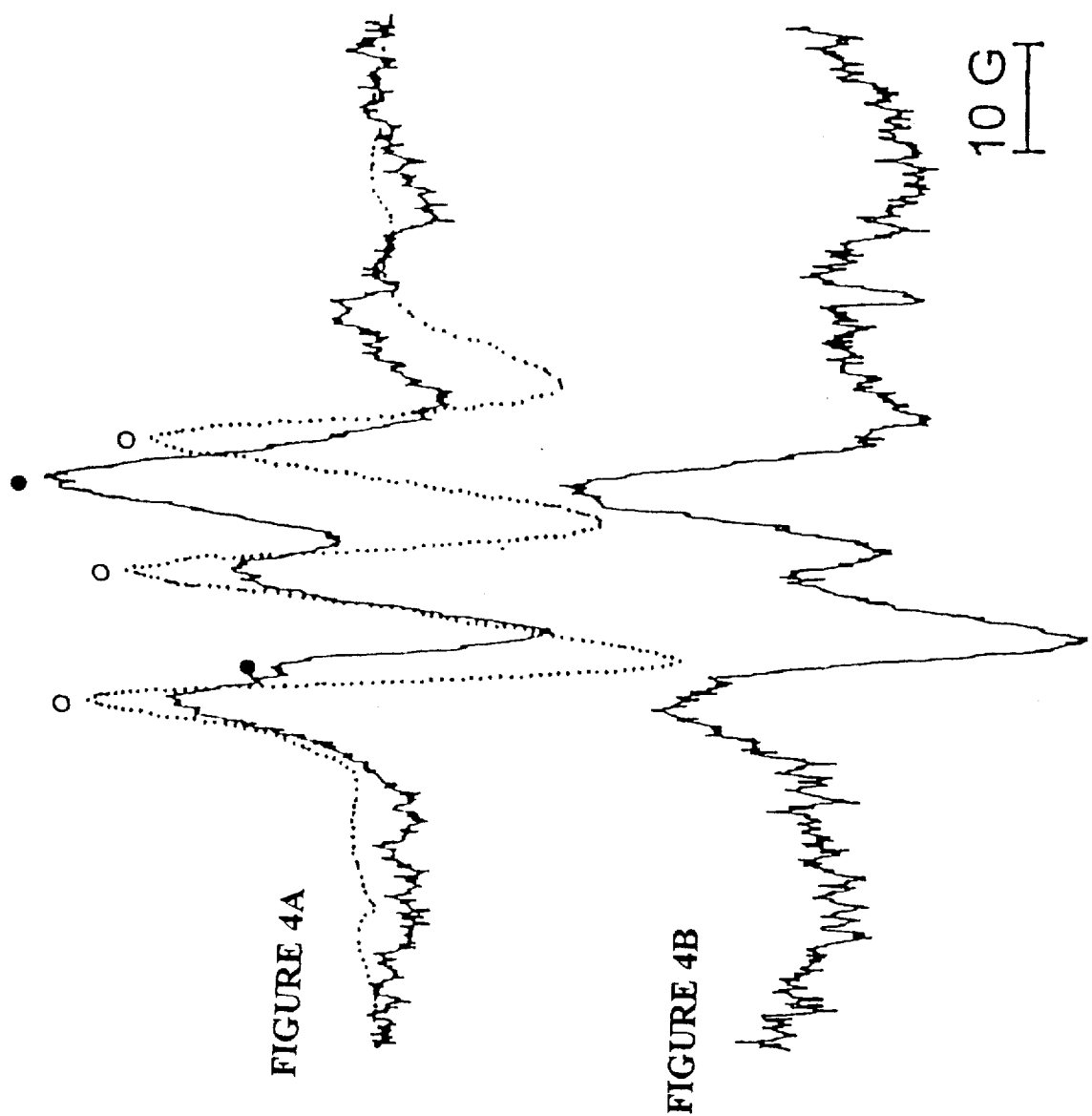

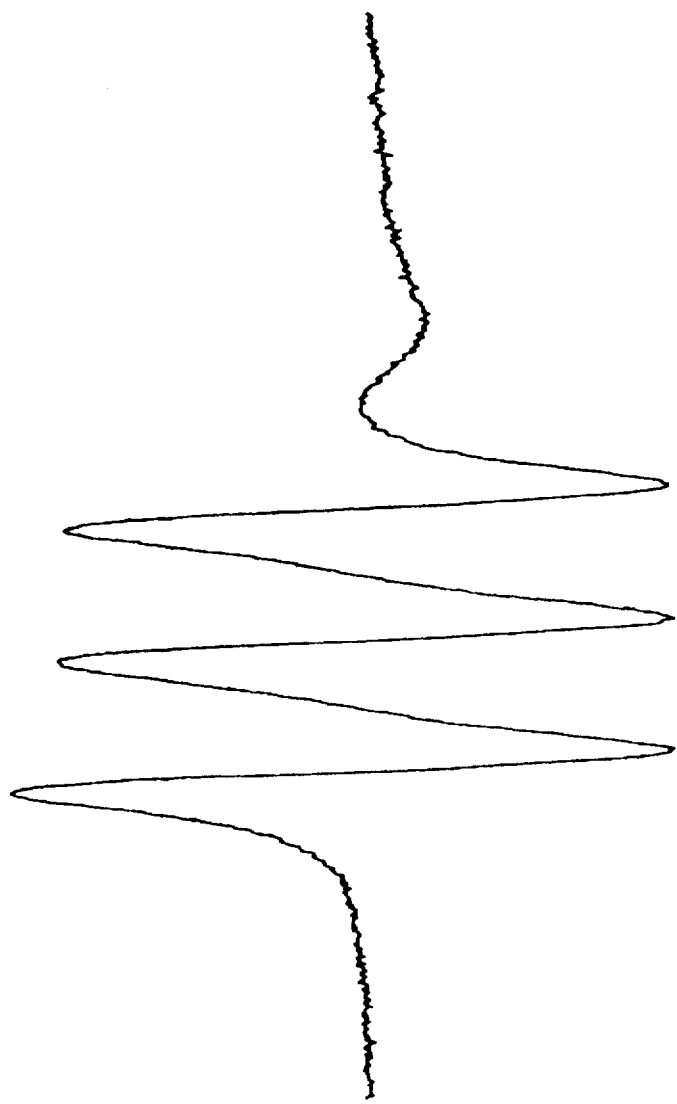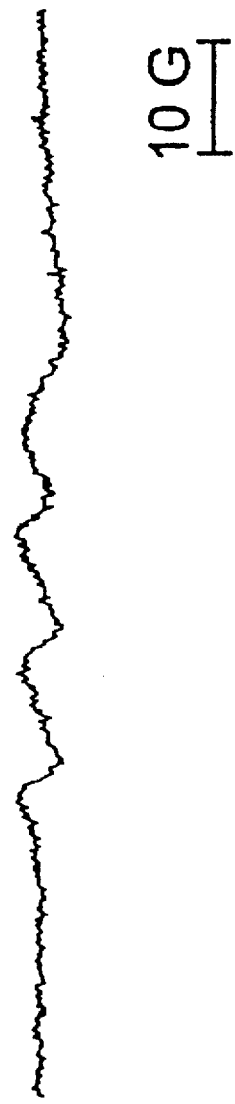
FIGURE 5A
FIGURE 5B

10 G

METHODS FOR IN VIVO REDUCTION OF NITRIC OXIDE LEVELS AND COMPOSITIONS USEFUL THEREFOR

ACKNOWLEDGEMENT

This invention was made with Government support under grant GM-35719, awarded by the National Institutes of Health. The Government has certain rights in the invention.

FIELD OF THE INVENTION

The present invention relates to methods for reducing nitric oxide levels in mammals. In a particular aspect, the present invention relates to methods for reducing nitric oxide levels in mammals by administration of dithiocarbamate-metal complexes as scavengers of nitric oxide in hosts afflicted with inflammatory or infectious diseases. In a further aspect, the present invention relates to compositions and formulations useful in the methods disclosed herein.

BACKGROUND OF THE INVENTION

Nitric oxide (·NO) is a free-radical cell messenger with numerous biological functions, including regulation of vascular tone, regulation of cellular signaling in the brain, and killing of pathogens by way of non-specific immune response (see, for example, Ignarro, L. J., *Ann. Rev. Toxicol* 30:535–560 (1990); Moncada, S., *Acta. Physiol. Scand.* 145:201–227 (1992); and Lowenstein and Snyder, *Cell* 70:705–707 (1992)). Nitric oxide is the product of the five-electron enzymatic oxidation of one of the chemically equivalent guanidino nitrogens of L-arginine. This oxidation is catalyzed by the enzyme, nitric oxide synthase. Two major types of nitric oxide synthase, constitutive and inducible enzymes, have been identified.

Constitutive ·NO synthase is present in the endothelium, where ·NO, a potent vasodilator, is continuously generated at low concentrations to regulate blood pressure and vascular tone. Inducible ·NO synthase is present in many cell types, including macrophages, neutrophils and leukocytes, as well as hepatocytes, vascular endothelial and smooth muscle cells. The latter ·NO synthase is induced by lipopolysaccharide (LPS) and cytokines, and produces ·NO at high concentrations for several days, serving important roles in non-specific immunity against inflammation and infection (Kilbourn and Griffith, *J. Natl. Cancer Instit.*, 84:827–831, (1992); Moncada and Higga, *N. Eng. J. Med.*, 329:2002–2012, (1993)). In the case of severe infection, overproduction of ·NO and cytokines can lead to life-threatening hypotension, multiple organ failure and eventually death (St. John and Dorinsky, *Chest.* 103:932–943 (1993)).

In blood, ·NO produced by the endothelium diffuses isotropically through all directions into adjacent tissues. As ·NO diffuses into the vascular smooth muscle, it binds to guanylate cyclase enzyme, which catalyzes the production of cGMP, and induces vasodilation (see, for example, Ignarro, L. J., supra; Moncada, S., supra; and Lowenstein and Snyder, supra). On the other hand, as ·NO diffuses into the blood circulation, it reacts with hemoglobin in red blood cells to yield nitrate and methemoglobin (Kelm and Schrader, *Circ. Res.* 66:1561–1575 (1990)). Nitrate is eliminated via renal excretion and methemoglobin is enzymatically converted back into hemoglobin by methemoglobin reductase in red blood cells. It is therefore not surprising that serum nitrate levels are increased in cytokine-induced and septic shock in animals and humans (see, for example, Nava et al., *J. Cardiovasc. Pharmacol.* 20(Suppl. 12):S132–134 (1992); Hibbs et al., *J. Clin. Invest.* 89:867–877 (1992); and Evans et al., *Circulatory Shock* 41:77–81 (1993)).

Nitric oxide overproduction has been shown to cause systemic hypotension induced by LPS and cytokines (e.g., interleukin-1 (IL-1), interleukin-2 (IL-2), tumor necrosis factor (TNF) and interferons) (Kilbourn and Griffith, supra, Moncada and Higgs, supra). Agents which inhibit the production of ·NO (by inhibiting the action of nitric oxide synthase) have been studied as a means to treat systemic hypotension due to ·NO overproduction. For example, $N^G$-monomethyl-L-arginine (NMMA), a competitive inhibitor of the nitric oxide biosynthetic pathway, was observed (upon intravenous injection) to reverse LPS-induced hypotension in animals (Aisaka et al., *Biochem. Biophys. Res. Commun.*, 60:881–886 (1989); Rees, et al., *Proc. Natl. Acad. Sci. USA*, 86:3375–3379, (1989)). However, as noted in many recent reports, the inhibition of ·NO synthase enzyme is detrimental to the subject. See, for example, Henderson et al., in Arch. Surg. 129:1271–1275 (1994), Hambrecht et al., in J. Leuk. Biol. 52:390–394 (1992), Luss et al., in Biochem. and Biophys. Res. Comm. 204:635–640 (1994), Robertson et al., in Arch. Surg. 129:149–156 (1994), Statman et al., in J. Surg. Res. 57:93–98 (1994), and Minnard et al., in Arch. Surg. 129:142–148 (1994).

Accordingly, there is still a need in the art to effectively treat systemic hypotension associated with ·NO overproduction, such as septic shock.

BRIEF DESCRIPTION OF THE INVENTION

In accordance with the present invention, methods have been developed for the in vivo reduction of nitric oxide levels. In contrast to the inhibitory approach described in the prior art (see references cited above), the present invention employs a scavenging approach whereby overproduced nitric oxide is bound in vivo to a suitable nitric oxide scavenger. The resulting complex renders the nitric oxide harmless, and is eventually excreted in the urine of the host. Further in accordance with the present invention, there have been developed compositions and formulations useful for carrying out the above-described methods.

An exemplary nitric oxide scavenger contemplated for use in the practice of the present invention is a dithiocarbamate-ferrous iron complex. This complex binds to ·NO, forming a stable, water-soluble dithiocarbamate-iron-NO complex having a characteristic three-line spectrum (indicative of a mononitrosyl-Fe complex) which can readily be detected at ambient temperatures by electron paramagnetic resonance (EPR) spectroscopy (See Komarov et al., in *Biochem. Biophys. Res. Commun.*, 195:1191–1198 (1993); Lai and Komarov, *FEBS Lett.*, 345:120–124, (1994)). This method of detecting ·NO in body fluids in real time has recently been described by Lai in U.S. Pat. No. 5,358,703, incorporated by reference herein. The present invention relates to methods for reducing in vivo levels of ·NO as a means of treating subjects afflicted with inflammatory and/or infectious disease. Dithiocarbamate-containing nitric oxide scavengers are administered to a host in need of such treatment; these scavengers interact with in vivo produced ·NO, forming a stable dithiocarbamate-metal-NO complex. Whereas free ·NO is a potent vasodilator, the ·NO chelated with dithiocarbamate-iron complexes is not. The NO-containing complex is then filtered through the kidneys, concentrated in the urine, and eventually excreted by the subject, thereby reducing in vivo ·NO levels.

BRIEF DESCRIPTION OF THE FIGURES

FIG. 1A presents results where [(MGD)$_2$/Fe] complex above was injected.

FIG. 1B presents results where [(MGD)$_2$/Fe] complex and NMMA were injected.

FIG. 1C presents results where [(MGD)$_2$/Fe] complex and dexamethasone were injected.

FIG. 2A presents results where [(MGD)$_2$/Fe] complex and 10 mg of $^{15}$N-arginine were injected.

FIG. 2B presents results where [(MGD)$_2$/Fe] complex and 5 mg of $^{15}$N-arginine were injected.

FIG. 3 presents in vivo 3.5-GHz EPR spectra of the [(MGD)$_2$/Fe-NO] complex in the circulation of the mouse tail. At 6 hours after LPS administration, the mice were injected with 10 mg of $^{15}$N-arginine in saline and 0.4 mL of the [(MGD)$_2$/Fe] complex. The in vivo S-band EPR spectra were recorded 2 hours after the [(MGD)$_2$/Fe] administration (the solid lines).

FIG. 3A exhibits a characteristic two-line spectrum of the [(MGD)$_2$/Fe-$^{15}$NO] complex (●). The dotted line spectrum of the [(MGD)$_2$/Fe-$^{14}$NO] complex in a (○) was obtained when $^{15}$N-arginine was omitted from the above injection solutions.

FIG. 3B illustrates the ex vivo X-band EPR spectrum of whole blood obtained from the $^{15}$N-arginine treated mice.

FIG. 4 presents ex vivo 3.5-GHz EPR spectra of [(MGD)$_2$/Fe-$^{15}$NO] and [(MGD)$_2$/Fe-$^{14}$NO] complexes detected in various tissues of LPS-treated mice after intravenous injection of $^{15}$N-arginine. Six hours after LPS administration, the mice were injected with 10 mg of $^{15}$N-arginine in saline and 0.4 ml of the [(MGD)$_2$/Fe] complex (326 mg/Kg of MGD and 34 mg/Kg of FeSO$_4$). Two hours after administration of the [(MGD)$_2$/Fe] complex, the mice were sacrificed and wet tissues transferred to quartz tubes (i.d. 2 mm) for EPR measurement at 22° C.

FIG. 4A presents spectra obtained from liver tissue. The two-line spectrum of the [(MGD)$_2$/Fe-$^{15}$NO] complex (●) is superimposed with the three-line spectrum of the [(MGD)$_2$/Fe-$^{14}$NO] complex (○). The dotted three-line spectrum of the [(MGD)$_2$/Fe-$^{14}$NO] complex was obtained when $^{15}$N-arginine was omitted from the injection solutions. Each spectrum was an average of nine 30-s scans.

FIG. 4B presents spectra obtained from kidney tissue. The spectrum shown was the average of nine 30-s scans.

FIG. 5 is a graphical presentation of the effect of NMMA on ex vivo 9.5-GHz EPR spectra of the [(MGD)$_2$/Fe-NO] complex in the urine of LPS-treated mice. At 6 hours after LPS treatment, the mice were injected with 0.4 mL of the [(MGD)$_2$/Fe] complex (326 mg/Kg of MGD and 34 mg/Kg of FeSO$_4$), with or without i.p. injection of NMMA (50 mg/kg). The mice were sacrificed 2 hours after injection of the [(MGD)$_2$/Fe] complex. The urine samples were collected and EPR measurements carried out at 22° C.

FIG. 5A presents results where [(MGD)$_2$/Fe] complex alone was injected.

FIG. 5B presents results where [(MGD)$_2$/Fe] complex and NMMA (50 mg/kg) were injected. Note: The NMMA administration inhibited in vivo NO production, thereby markedly reducing the signal intensity of the [(MGD)$_2$/Fe-NO] in the urine.

FIG. 6 presents ex vivo 9.5-GHz EPR spectra of [(MGD)$_2$/Fe-$^{15}$NO] and [(MGD)$_2$/Fe-$^{14}$NO] complexes in the urine of LPS-treated mice injected with $^{15}$N-arginine. Six hours after LPS administration, the mice were injected with 5 or 10 mg of $^{15}$N-arginine in saline and 0.4 ml of the [(MGD)$_2$/Fe] complex (326 mg/Kg of MGD and 34 mg/Kg of FeSO$_4$). Urine samples were collected two hours after administration of the [(MGD)$_2$/Fe] complex, and transferred to quartz tubes (i.d. 2 mm) for EPR measurement at 22° C.

DETAILED DESCRIPTION OF THE INVENTION

Figures 1A, 1B, 1C:
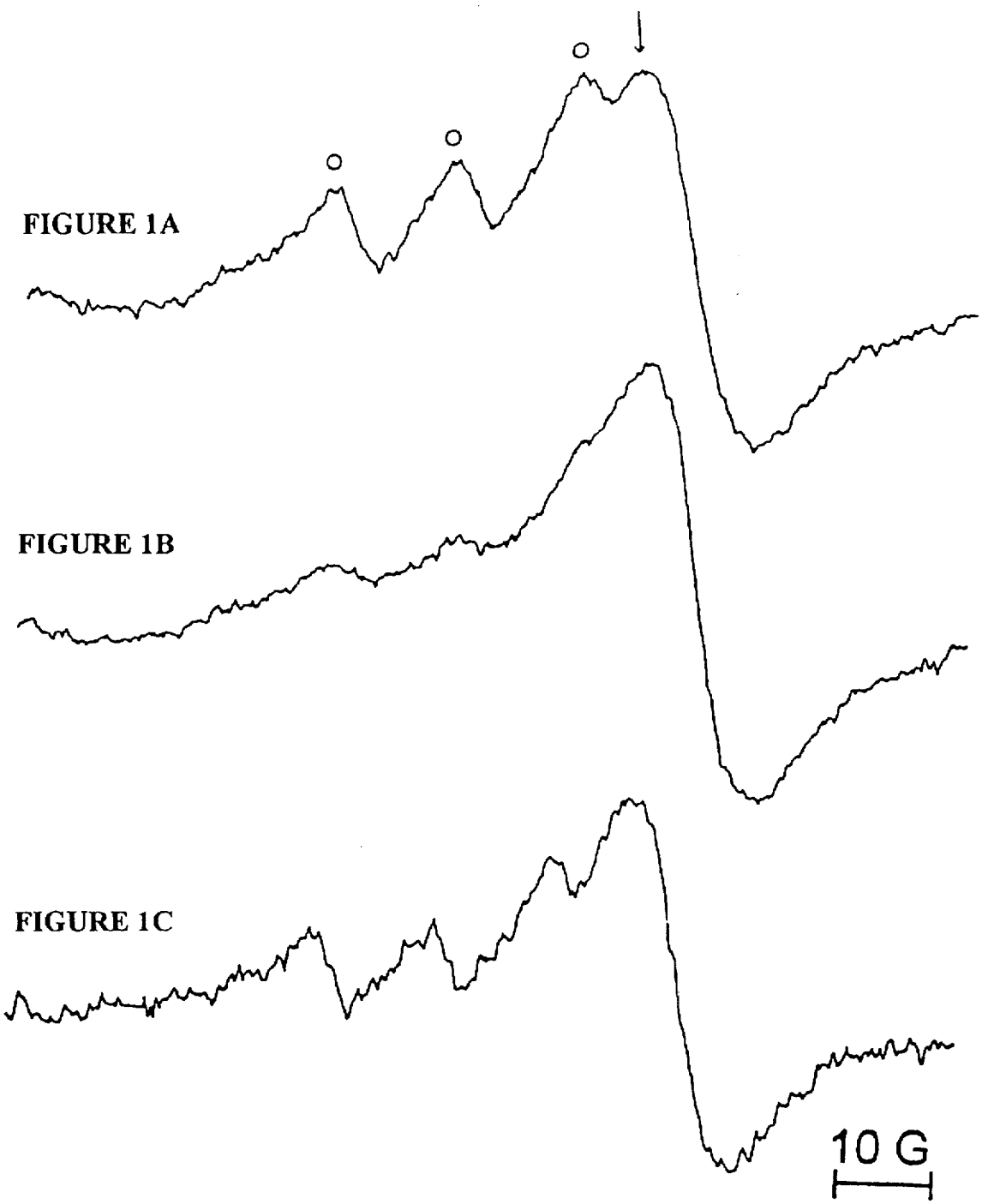
FIG. 1A, FIG. 1B and FIG. 1C illustrate illustrates the effects of ·NO inhibitors on ex-vivo 9.5-GHz EPR spectra of the [(MGD)$_2$/Fe-NO] complex (MGD is N-methyl-D-glucamine dithiocarbamate) detected in the urine of normal mice. The mice were injected subcutaneously with 0.4 mL of the [(MGD)$_2$/Fe] complex (326 mg/Kg of MGD and 34 mg/Kg of FeSO$_4$) (FIG. 1A), and in the presence of NMMA (50 mg/kg) (FIG. 1B), or of dexamethasone (3 mg/kg) (FIG. 1C). Details of the experimental protocols are described in the Examples. The animals were sacrificed at two hours after injections, and the urine samples collected were transferred to a quartz flat cell for EPR measurement at 22° C. The three-line spectrum of the [(MGD)$_2$/Fe] complex is indicated by open circles (○), and a broad EPR line which is part of the spectrum of the [(MGD)$_2$/Cu] complex is indicated by an arrow.

In accordance with the present invention, there are provided methods for the in vivo reduction of nitric oxide levels in a subject. Invention methods comprise:

administering to a subject an effective amount of at least one dithiocarbamate-containing nitric oxide scavenger.

Dithiocarbamate-containing nitric oxide scavengers contemplated for use in the practice of the present invention include any physiologically compatible derivative of the dithiocarbamate moiety (i.e., (R)$_2$N—C(S)—SH). Such compounds can be described with reference to the following generic structure:

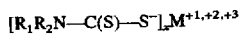

$[R_1R_2N—C(S)—S^-]_xM^{+1,+2,+3}$ wherein:

$R_1$ is selected from a $C_1$ up to $C_{12}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, aroyl, substituted aroyl, acyl, substituted acyl or $R_1$ and $R_2$ can cooperate to form a 5-, 6- or 7-membered ring including N, R, and $R_2$, $R_2$ is selected from a $C_1$ up to $C_6$ alkyl or substituted alkyl, or $R_2$ can cooperate with $R_1$ to form a 5-, 6- or 7-membered ring including N, $R_2$ and $R_1$, x is 1 or 2, and M is a monovalent cation when x is 1, or M is a physiologically compatible divalent or trivalent transition metal cation when x is 2.

When $R_1$ and $R_2$ cooperate to form a 5-, 6- or 7-membered ring, the combination of $R_1$ and $R_2$ can be a variety of saturated or unsaturated 4, 5 or 6 atom bridging species selected from alkenylene or —O—, —S—, —C(O)— and/or —N(R)— containing alkylene moieties, wherein R is hydrogen or a lower alkyl moiety.

Monovalent cations contemplated for incorporation into the above compounds include $H^+$, $Na^+$, $NH_4^+$, tetraalkyl ammonium, and the like. Physiologically compatible divalent or trivalent transition metal cations contemplated for incorporation into the above compounds include charged forms of iron, cobalt, copper, manganese, or the like (e.g., $Fe^{+2}$, $Fe^{+3}$, $Co^{+2}$, $Co^{+3}$, $Cu^{+2}$, $Mn^{+2}$ or $Mn^+3$).

As employed herein, "substituted alkyl" comprises alkyl groups further bearing one or more substituents selected from hydroxy, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, amino, amido, —C(O)H, acyl, oxyacyl, carboxyl, carbamate, sulfonyl, sulfonamide, sulfuryl, and the like.

As employed herein, "cycloalkyl" refers to cyclic ring-containing groups containing in the range of about 3 up to 8 carbon atoms, and "substituted cycloalkyl" refers to cycloalkyl groups further bearing one or more substituents as set forth above.

As employed herein, "alkenyl" refers to straight or branched chain hydrocarbyl groups having at least one carbon-carbon double bond, and having in the range of about 2 up to 12 carbon atoms, and "substituted alkenyl" refers to alkenyl groups further bearing one or more substituents as set forth above.

As employed herein, "alkynyl" refers to straight or branched chain hydrocarbyl groups having at least one carbon-carbon triple bond, and having in the range of about 2 up to 12 carbon atoms, and "substituted alkynyl" refers to alkynyl groups further bearing one or more substituents as set forth above.

As employed herein, "aryl" refers to aromatic groups having in the range of 6 up to 14 carbon atoms and "substituted aryl" refers to aryl groups further bearing one or more substituents as set forth above.

As employed herein, "alkylaryl" refers to alkyl-substituted aryl groups and "substituted alkylaryl" refers to alkylaryl groups further bearing one or more substituents as set forth above.

As employed herein, "arylalkyl" refers to aryl-substituted alkyl groups and "substituted arylalkyl" refers to arylalkyl groups further bearing one or more substituents as set forth above.

As employed herein, "arylalkenyl" refers to aryl-substituted alkenyl groups and "substituted arylalkenyl" refers to arylalkenyl groups further bearing one or more substituents as set forth above.

As employed herein, "arylalkynyl" refers to aryl-substituted alkynyl groups and "substituted arylalkynyl" refers to arylalkynyl groups further bearing one or more substituents as set forth above.

As employed herein, "aroyl" refers to aryl-carbonyl species such as benzoyl and "substituted aroyl" refers to aroyl groups further bearing one or more substituents as set forth above.

As employed herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As employed herein, "acyl" refers to alkyl-carbonyl species.

As employed herein, "halogen" refers to fluoride, chloride, bromide or iodide atoms.

In accordance with another embodiment of the present invention, there are provided methods for treating nitric oxide overproduction in a subject. Invention methods comprise:

administering to a subject an effective amount of at least one dithiocarbamate-containing nitric oxide scavenger.

Nitric oxide overproduction is associated with a wide range of disease states and/or indications, such as, for example, septic shock, ischemia, administration of cytokines, overexpression of cytokines, ulcers, inflammatory bowel disease (e.g., ulcerative colitis or Crohn's disease), diabetes, arthritis, asthma, Alzheimer's disease, Parkinson's disease, multiple sclerosis, cirrhosis, allograft rejection, encephalomyelitis, meningitis, pancreatitis, peritonitis, vasculitis, lymphocytic choriomeningitis, glomerulonephritis, uveitis, ileitis, liver inflammation, renal inflammation, hemorrhagic shock, anaphylactic shock, burn, infection (including bacterial, viral, fungal and parasitic infections), and the like.

With particular reference to cytokine therapy, the invention method will find widespread use because cytokine therapy (with consequent induction of nitric oxide overproduction) is commonly used in the treatment of cancer and AIDS patients. Systemic hypotension due to the induction of ·NO overproduction is a dose-limiting side effect of cytokine therapy. Thus, a large patient population exists which will benefit from the invention method.

Presently preferred indications for treatment in accordance with the present invention include septic shock, ischemia, administration of IL-1, administration of IL-2, administration of IL-6, administration of IL-12, administration of tumor necrosis factor, administration of interferon-gamma, ulcers, ulcerative colitis, diabetes, arthritis, asthma, Alzheimer's disease, Parkinson's disease, multiple sclerosis, cirrhosis or allograft rejection. Especially preferred indications for treatment in accordance with the present invention include nitric oxide overproduction associated with septic shock and nitric oxide overproduction associated with cytokine therapy.

In accordance with a particular aspect of the present invention, the dithiocarbamate-containing nitric oxide scavenger is administered in combination with a cytokine (e.g., IL-1, IL-2, IL-6, IL-12, TNF or interferon-γ), an antibiotic (e.g., gentamicin, tobramycin, amikacin, piperacillin, clindamycin, cefoxitin or vancomycin, or mixtures thereof), a vasoactive agent (e.g., a catecholamine, noradrenaline, dopamine or dobutamine), or mixtures thereof. In this way, the detrimental side effects of many of the above-noted pharmaceutical agents (e.g., systemic hypotension) can be prevented or reduced by the dithiocarbamate-containing nitric oxide scavenger.

Those of skill in the art recognize that the dithiocarbamate-containing nitric oxide scavengers described herein can be delivered in a variety of ways, such as, for example, orally, intravenously, subcutaneously, parenterally, rectally, by inhalation, and the like.

Since individual subjects may present a wide variation in severity of symptoms and each drug has its unique therapeutic characteristics, the precise mode of administration and dosage employed for each subject is left to the discretion of the practitioner.

In accordance with still another embodiment of the present invention, there are provided physiologically active composition(s) comprising a compound having the structure I or the structure II, as described hereinafter, in a suitable vehicle rendering said compound amenable to oral delivery, transdermal delivery, intravenous delivery, intramuscular delivery, topical delivery, nasal delivery, and the like.

Depending on the mode of delivery employed, the dithiocarbamate-containing nitric oxide scavenger can be delivered in a variety of pharmaceutically acceptable forms. For example, the scavenger can be delivered in the form of a solid, solution, emulsion, dispersion, micelle, liposome, and the like.

Pharmaceutical compositions of the present invention can be used in the form of a solid, a solution, an emulsion, a dispersion, a micelle, a liposome, and the like, wherein the resulting composition contains one or more of the compounds of the present invention, as an active ingredient, in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. The active compound (i.e., compounds of structure I or structure II as described herein) is included in the pharmaceutical composition in an amount sufficient to produce the desired effect upon the process or condition of diseases.

Pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing the active ingredient in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874, to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example, peanut oil, liquid paraffin, or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Compounds contemplated for use in the practice of the present invention may also be administered in the form of suppositories for rectal administration of the drug. These compositions may be prepared by mixing the drug with a suitable non-irritating excipient, such as cocoa butter, synthetic glyceride esters of polyethylene glycols, which are solid at ordinary temperatures, but liquify and/or dissolve in the rectal cavity to release the drug.

Since individual subjects may present a wide variation in severity of symptoms and each drug has its unique therapeutic characteristics, it is up to the practitioner to determine a subject's response to treatment and vary the dosages accordingly.

Typical daily doses, in general, lie within the range of from about 10 µg up to about 100 mg per kg body weight, and, preferably within the range of from 50 µg to 10 mg per kg body weight and can be administered up to four times daily. The daily IV dose lies within the range of from about 1 µg to about 100 mg per kg body weight, and, preferably, within the range of from 10 µg to 10 mg per kg body weight.

In accordance with yet another embodiment of the present invention, there are provided compounds having the structure I:

$$R_1R_2N\text{—}C(S)\text{—}S^-M^+ \qquad (I)$$

wherein:

$R_1$ and $R_2$ are as defined above, and

M is a monovalent cation, provided, however, that the following compounds are excluded from the definition of Formula I, i.e., when $R_1$ is ethyl, $R_2$ is not ethyl; or when $R_1$ is $CH_2(CHOH)_4CH_2OH$, $R_2$ is not methyl, isoamyl, benzyl, 4-methylbenzyl or p-isopropylbenzyl; or when $R_1$ is $CH_2CO_2^-$, $R_2$ is not $CH_2CO_2^-$; or when $R_1$ is $CO_2^-$, $R_2$ is not $CH_3$; or when $R_1$ is $CH_2CH_2$—OH, $R_2$ is not $CH_2CH_2$—OH; or when $R_1$ and $R_2$ combined, together with the carbamate nitrogen, form a pyrrolidinyl-2-carboxylate.

In accordance with still another embodiment of the present invention, there are provided compounds having the structure II:

$$[R_1R_2N\text{—}C(S)\text{—}S^-]_2\ M^{+2,+3} \qquad (II)$$

wherein:

$R_1$ and $R_2$ are as defined above, and

M is a physiologically compatible divalent or trivalent transition metal cation, provided, however, that the following compounds are excluded from the definition of Formula II, i.e., when $R_1$ is ethyl, $R_2$ is not ethyl; or when $R_1$ is $CH_2(CHOH)_4CH_2OH$, $R_2$ is not methyl, isoamyl, benzyl, 4-methylbenzyl or p-isopropylbenzyl; or when $R_1$ is $CH_2CO_2$, $R_2$ is not $CH_2CO_2^-$; or when $R_1$ is $CO_2^-$, $R_2$ is not $CH_3$; or when $R_1$ is $CH_2CH_2$—OH, $R_2$ is not $CH_2CH_2$—OH; or when $R_1$ and $R_2$ combined, together with the carbamate nitrogen, form a pyrrolidinyl-2-carboxylate.

Presently preferred compounds having the structure II are those wherein:

$R_1$=a $C_1$ up to $C_{12}$ alkyl, substituted alkyl, alkenyl, substituted alkenyl, alkynyl or substituted alkynyl, wherein the substituents are selected from carboxyl, —C(O)H, oxyacyl, phenol, phenoxy, pyridinyl, pyrrolidinyl, amino, amido, hydroxy, nitro or sulfuryl, $R_2$=a $C_1$ up to $C_4$ alkyl or substituted alkyl, and $M=Fe^{+2}$ or $Fe^{+3}$.

Especially preferred compounds having the structure II are those wherein:

$R_1$=a $C_2$ up to $C_8$ alkyl or substituted alkyl, wherein the substituents are selected from carboxyl, acetyl, pyridinyl, pyrrolidinyl, amino, amido, hydroxy or nitro, $R_2$=methyl, ethyl, propyl or butyl, and $M=Fe^{+2}$.

The presently most preferred compounds having the structure II are those wherein:

$R_1$ a $C_2$ up to $C_8$ alkyl or substituted alkyl, wherein the substituents are selected from carboxyl, acetyl, amido or hydroxy, $R_2$=methyl, ethyl, propyl or butyl, and $M=Fe^{+2}$.

The invention will now be described in greater detail by reference to the following non-limiting examples.

EXAMPLE 1

ICR mice (female, 20–30 g) were supplied by Harlan Sprague-Dawley (Indianapolis, Ind.).

Dexamethasone, lipopolysaccharide (LPS; *E. coli* O26:B6) and acetylcholine chloride were obtained from Sigma (St. Louis, Mo.). $^{15}N_2$-guanido-L-arginine ($^{15}N$-arginine) was purchased from Cambridge Isotope Laboratories (Woburn, Mass.). $N^G$-monomethyl-L-arginine (NMMA) was obtained from Calbiochem (San Diego, Calif.). Methoxyflurane was obtained from Pitman-Moore (Mundelein, Ill.).

Pure ·NO gas was purchased from Matheson (Joliet, Ill.) and pure argon gas was obtained from Airco (Murray Hill, N.J.). Saturated ·NO solution in water was prepared by following the method of Kelm and Schrader, supra.

The concentration of the saturated ·NO solution is 2.0 mM, as verified by an ISO-NO meter from World Precision Instruments (Sarasota, Fla.). $NO_2^-$ was measured by a calorimetric assay (Green et al., *Anal. Biochem.* 126:131–138 (1982)). $NO_3^-$ was first converted to $NO_2^-$ by *E. coli* nitrate reductase (Bartholomew, B., *Fd. Chem. Toxic.* 22:541–543 (1984)) and measured as described above.

N-Methyl-D-glucamine and carbon disulfide were obtained from Aldrich (Milwaukee, Wis.). N-Methyl-D-glucamine dithiocarbamate (MGD) was synthesized by following the method of Shinobu et al. (*Acta Pharmacol. Toxicol.* 54:189–194 (1984)).

EXAMPLE 2

EPR measurement of nitric oxide levels

A. In vivo measurement of [(MGD)$_2$/FE-NO] levels in the circulation of the LPS-treated mice.

Noninvasive in vivo EPR spectra were recorded with an EPR spectrometer equipped with an S-band microwave bridge and a low-frequency loop-gap resonator with a 4-mm loop with a length of 1 cm, operating at 3.5 GHz (Froncisz and Hyde, *J. Magn. Reson.* 47:515–521 (1982)). Instrument settings include 100-G field scan, 30-s scan time, 0.1-s time constant, 2.5-G modulation amplitude, 100-KHz modulation frequency and 25-mW microwave power. The measured unloaded Q of the empty resonator was 3000 and the loaded Q was 400 (with the presence of the mouse tail). Other instrument settings and experimental conditions have been described previously (Komarov et al., supra and Lai and Komarov, supra).

For measurement of $^{15}$NO production, at 6 h after i.v. injection of LPS (6 mg/mouse) via the lateral tail vein, the mice were anesthetized with methoxyflurane prior to subcutaneous injections of $^{15}$N-arginine (5 or 10 mg per mouse) in saline, and of 0.4 ml of the [(MGD)$_2$/Fe] complex (326 mg/kg of MGD and 34 mg/kg of FeSO$_4$) in water. Injections of [(MGD)$_2$/Fe] complex at levels up to 1% body weight did not affect the survival of the mice (Lai and Komarov, supra). Immediately after injection, the mouse housed in a plexiglass restraining tube was transferred to the S-band EPR spectrometer and the tail of the mouse was immobilized by taping down with a thin and narrow plexiglass stick and then placed inside the resonator; no anesthetic agent was used. The in vivo EPR signal was recorded at 2 h after the injection of the [(MGD)$_2$/Fe] complex (Lai and Komarov, supra).

For inhibition experiments, at 6 h after LPS treatment, mice were injected intraperitoneally with an aliquot of 50 mg/kg N-monomethyl-L-arginine (NMMA) in saline. NMMA is an inhibitor of both constitutive and inducible synthase activities (Aisaka et al., supra and Rees et al., supra). In other experiments, at 1.5 h prior to LPS challenge, mice were injected intravenously with 3 mg/kg dexamethasone in saline. Dexamethasone is an inhibitor of inducible ·NO synthase, but not constitutive ·NO synthase (Rees et al., *Biochem. Biophys. Res. Commun.* 173:541–547 (1990)). The in vivo EPR signal was also recorded at 2 h after the injection of [(MGD)$_2$/Fe] complex (Lai and Komarov, supra).

B. Ex vivo measurements of [(MGD)$_2$/Fe-NO] levels in the urine of normal mice.

Normal mice housed in a restraining tube were injected subcutaneously with 0.4 ml of the [(MGD)$_2$/Fe] complex (326 mg/Kg of MGD and 34 mg/Kg of FeSO$_4$). After 2 h, the animals were sacrificed and the urine samples were collected from the urinary bladder. The urine sample, which was dark brown (characteristic of the presence of [(MGD)$_2$/Fe] complex), was transferred to a quartz flat cell for EPR measurement. The spectra were recorded at 22° C. with an X-band EPR spectrometer, operating at 9.5 GHz. Instrument settings include 100-G field scan, 4-min scan time, 0.5-s time constant, 2.5-G modulation amplitude, 100-Hz modulation frequency and 100-mW microwave power. The concentrations of the [(MGD)$_2$/Fe-NO] complex in the urine samples were calculated by comparing the signal intensities obtained from the samples to the signal intensity of a standard solution containing 0.1 mM of the [(MGD)$_2$/Fe-NO] complex.

For inhibition experiments, mice were injected intraperitoneally with 50 mg/kg NMMA in saline immediately after the injection of the [(MGD)$_2$/Fe] complex. In other experiments, mice were injected intravenously with 3 mg/kg dexamethasone in saline about 1.5 h before the injection of the [(MGD)$_2$/Fe] complex. For measurement of $^{15}$NO production in normal mice, mice were injected subcutaneously with $^{15}$N-arginine (5 or 10 mg/mouse) in saline immediately before the injection of the [(MGD)$_2$/Fe] complex. Acetylcholine chloride (Sigma) in saline was freshly prepared prior to subcutaneous injection at a dose of 67 mg/kg.

C. Ex vivo measurement of [(MGD)$_2$/Fe-NO] levels in the urine of LPS-treated mice.

At 0, 2, 4, 6 or 8 h after LPS treatment (6 mg/mouse; at least three animals in each group), the mice housed in a restraining tube were anesthetized with methoxyflurane prior to subcutaneous injection with 0.4 ml of the [(MGD)$_2$/Fe] complex (326 mg/Kg of MGD and 34 mg/Kg of FeSO$_4$). After 2 h, the mouse was sacrificed and the urine sample was collected from the urinary bladder, and immediately transferred to a quartz flat cell for X-band EPR measurement as described above in Example 2B. Inhibition experiments with NMMA or dexamethasone were performed as described above in Example 2A, except that the mice were treated with LPS prior to following the protocols for ·NO inhibition experiments. The procedures for S-band EPR measurement of wet tissues and blood samples were as described previously (Lai and Komarov, supra).

EXAMPLE 3

Detection of the [(MGD)$_2$/Fe-NO] complex in the urine of normal mice

At 2 h after subcutaneous injection of an aliquot (0.4 ml) of the [(MGD)$_2$/Fe] complex (326 mg/Kg of MGD and 34 mg/Kg of FeSO$_4$) into normal mice (A) (and also in the presence of NMMA (50 mg/kg) (B), or of dexamethasone (3 mg/kg) (C)), the animals were sacrificed and the urine samples collected and transferred to a quartz flat cell for X-band (9.5 GHz) EPR measurement at 22° C. The spectrum of the urine samples was found to be composed of two components, a three-line spectrum ($\alpha^N$=12.5 G and $g_{ISO}$= 2.04) characteristic of the [(MGD)$_2$/Fe-NO] complex, and a strong broad signal (See FIG. 1A). The strong broad signal is part of the EPR spectrum of the [(MGD)$_2$/Cu] complex present in the urine, resulting from the chelation of urinary copper by the excreted MGD molecule. The concentration of the [(MGD)$_2$/Fe-NO] complex detected in the urine sample of normal mice is estimated to be 1.3 µM (see Table 1).

TABLE 1

Quantitation of the amounts of [(MGD)$_2$/Fe—NO] present in mouse urine under various conditions

| Conditions | [(MGD)$_2$/Fe—NO], µM[a] |
|---|---|
| Controls | 1.3 ± 0.2 (8)[b] |
| + NMMA (50 mg/kg) | 0.4 ± 0.3 (8)* |
| + Acetylcholine (67 mg/kg) | 3.9 ± 0.8 (3)* |
| + Dexamethasone (3 mg/kg) | 1.4 ± 0.3 (7) |

[a]The amounts of the [(MGD)$_2$/Fe—NO] complex in mouse urine were calculated by comparing the EPR signal intensities of mouse urine with the signal intensity of a standard solution containing known concentration of [(MGD)$_2$/Fe—NO].
[b]The data presented are mean ± S.E. (number of mice).
*P < 0.05 compared with controls.

Simultaneous injection of [(MGD)$_2$/Fe] and NMMA markedly reduced the [(MGD)$_2$/Fe-NO] signal in the urine samples, see FIG. 1B and Table 1. On the other hand, as noted in FIG. 1C and Table 1, injection of [(MGD)$_2$/Fe] into mice pretreated with dexamethasone produced negligible effects on the [(MGD)$_2$/Fe-NO] signal.

These results suggest that the ·NO detected in normal mouse urine in the form of the [(MGD)$_2$/Fe-NO] complex was produced by constitutive ·NO synthase, but not by inducible ·NO synthase.

To further verify this suggestion, the effect of acetylcholine, a vasodilatory agent which is known to effect the basal ·NO level, but not the inducible ·NO level (Aisaka et al., Biochem. Biophys. Res. Commun. 163:710–717 (1989); Whittle et al., Br. J. Pharmacol. 98:646–652 (1989); and Vicaut et al., J. Appl. Physiol. 77:536–533 (1994)), was tested on the urinary [(MGD)$_2$/Fe-NO] level of normal mice. Injection of acetylcholine was found to produce a 3-fold increase in urinary [(MGD)$_2$/Fe-NO] levels (see Table 1). This observation represents the first direct in vivo evidence to confirm that the endothelium-derived relaxation factor released by acetylcholine (the Furchgott phenomenon) is indeed nitric oxide.

The question is raised whether the ·NO detected in normal mouse urine (Example 3) and the ·NO trapped by the [(MGD)$_2$/Fe] complex (Table 1) is a result of the injection of the [(MGD)$_2$/Fe] complex. In other words, does the injection of the complex alone enhance the ·NO production in vivo? In the previous experiments, it has been shown that the intravenous injection of the [(MGD)$_2$/Fe] complex did not affect the mean arterial pressure of mice (Komarov, et al. supra), suggesting that the complex by itself does not seem to affect the in vivo ·NO production.

EXAMPLE 4

It is well established in the art that L-arginine is converted into ·NO and citrulline by ·NO synthase enzymes (Ignarro, L. J., supra; Moncada, S., supra; and Lowenstein and Snyder, supra). To determine the origin of ·NO detected in normal mouse urine, $^{15}$N-arginine (10 mg/mouse) and [(MGD)$_2$/Fe] were injected simultaneously, and the EPR signal in the resulting urine sample was measured, as described above. Thus, mice were injected with 0.4 ml of the [(MGD)$_2$/Fe] complex (326 mg/Kg of MGD and 34 mg/Kg of FeSO$_4$) with (A) 10 mg $^{15}$N-arginine or (B) 5 mg of $^{15}$N-arginine. The animals were sacrificed at 2 h after injection, and the urine samples were transferred to a quartz flat cell for EPR measurement at 22° C.

It was reasoned that if the ·NO detected in normal mouse urine comes from the arginine-NO synthase pathway, upon injection of $^{15}$N-arginine, one should expect to detect the $^{15}$NO in the form of the [(MGD)$_2$/Fe-$^{15}$NO] complex in the urine. This indeed was the case as seen by EPR, in which the two-line spectrum of the [(MGD)$_2$/Fe-$^{15}$NO] complex was detected in the urine, along with a weak three-line spectrum of the [(MGD)$_2$/Fe-$^{14}$NO] complex (FIG. 2A, the solid lines); the $^{14}$NO was generated by the same enzymatic pathway, except utilizing endogenous $^{14}$N-arginine as a substrate. This suggests that subcutaneously injected $^{15}$N-arginine competes effectively with endogenous $^{14}$N-arginine as a substrate for ·NO synthases. When $^{15}$N-arginine was omitted from the injection solution, the typical three-line spectrum of the [(MGD)$_2$/Fe-$^{14}$NO] complex became more visible (see FIG. 2A, dotted lines).

Figures 2A, 2B:
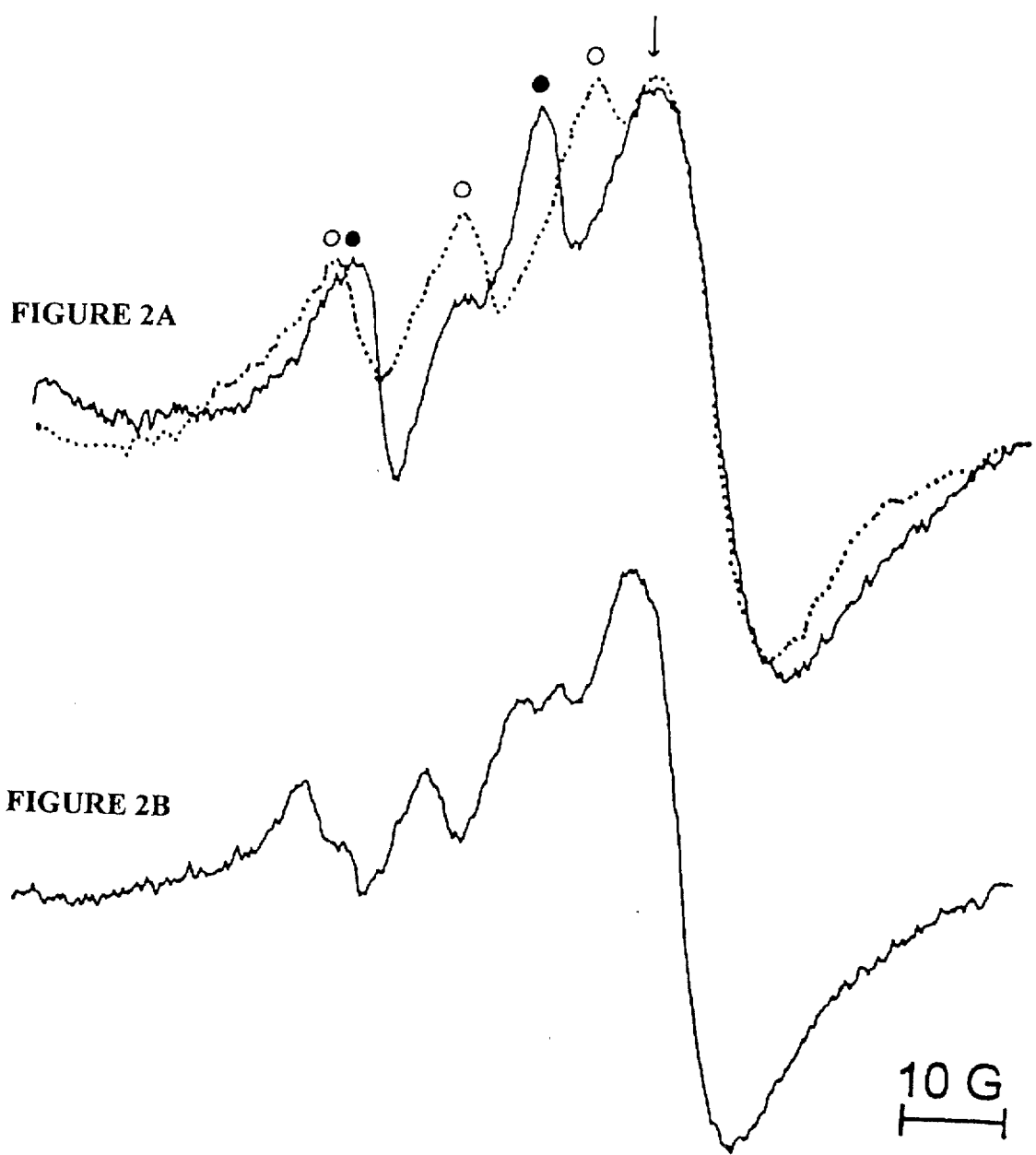
FIG. 2A and FIG. 2B present Ex-vivo 9.5 GHz EPR spectra of the [(MGD)$_2$/Fe-$^{15}$NO] and [(MGD)$_2$/Fe-$^{14}$NO] complexes present in the urine of normal mice injected with $^{15}$N-arginine. The mice were injected with 0.4 mL of the [(MGD)$_2$/Fe] complex (326 mg/Kg and 34 mg/Kg of FeSO$_4$) with (A) 10 mg $^{15}$N-arginine or (B) 5 mg $^{15}$N-arginine. The animals were sacrificed at two hours after injections, and the urine samples were transferred to a quartz flat cell for EPR measurement at 22° C. Note: The two-line spectrum of the [(MGD)/Fe-$^{15}$NO] complex is indicated by closed circles (●). The dotted lines of the [(MGD)$_2$/FE-$^{14}$NO] spectrum in A as indicated by open circles (○) were obtained without the injection of $^{15}$N-arginine. The receiver gain for A was 1.3 times higher than that of B and the rest of the experimental conditions were the same as described with respect to FIG. 1A, FIG. 1B and FIG. 1C.

On the other hand, when the amount of $^{15}$N-arginine injected (5 mg/mouse) was reduced by one-half, the signal intensity of the [(MGD)$_2$/Fe-$^{15}$NO] complex decreased compared to that of the [(MGD)$_2$/Fe-$^{14}$NO] complex (see FIG. 2B). Therefore, it can be concluded that the [(MGD)$_2$/Fe] complex injected subcutaneously into normal mice interacts with the ·NO produced in tissues through the arginine-constitutive ·NO synthase pathway to form the [(MGD)$_2$/Fe-NO] complex, which is eventually concentrated in the urine and excreted.

EXAMPLE 5

Detection of the [(MGD)$_2$/Fe-NO] complex in the blood circulation of LPS-treated mice It has previously been shown that upon bolus infusion of LPS (6 mg/mouse), mice are in septic-shock like conditions within 6 h, as indicated by a gradual fall in mean arterial pressure from 121±3 mm Hg to 85±7 mm Hg (Lai and Komarov, supra). In addition, it has been shown that at 6 h after LPS treatment, the in vivo three-line spectrum of the [(MGD)$_2$/Fe-NO] complex (wherein [(MGD)$_2$/Fe] is injected subcutaneously 2 h before EPR measurement) is observed in the circulation of the mouse tail, as detected by S-band EPR spectroscopy (Lai and Komarov, supra).

To further ascertain the chemical nature of ·NO detected in LPS-treated mice, $^{15}$N-arginine (10 mg/kg) was injected, together with 0.4 ml of the [(MGD)$_2$/Fe] spin-trapping reagent (326 mg/Kg of MGD and 34 mg/Kg of FeSO$_4$), into LPS-treated mice and measured in vivo by S-band EPR spectrum. The in vivo S-band EPR spectra were recorded 2 h after administration of the [(MGD)$_2$/Fe] complex.

Albeit weak, the in vivo two-line spectrum of the [(MGD)$_2$/Fe$^{15}$-NO] complex in the circulation of the mouse tail was clearly visible (FIG. 3A, the solid lines), further confirming that the detected ·NO in the form of the [(MGD)$_2$/Fe-NO] complex in LPS-treated mice was produced via the arginine-NO synthase pathway. The three-line spectrum typical of the [(MGD)$_2$/Fe-$^{14}$NO] complex was obtained when $^{15}$N-arginine was omitted (FIG. 3A, the dotted lines). The mice treated with $^{15}$N-arginine were sacrificed, and the whole blood obtained was transferred for X-band EPR measurement at 22° C. The EPR signal of the whole blood obtained from $^{15}$N-arginine treated mice (FIG. 3B) is identical to that of the solid lines of FIG. 3A. This suggests that the EPR signal in FIG. 3A or FIG. 3B is attributed to the [(MGD)$_2$/Fe-NO] complex circulating in the blood, rather than trapped in the tail muscle at or near the site of the injection.

The S-band EPR signal of the [(MGD)$_2$/Fe-$^{15}$NO] complex was also detected in various isolated tissues obtained from LPS-treated mice injected with the [(MGD)$_2$/Fe] complex and $^{15}$N-arginine (FIG. 4). Thus, the two-line spectrum characteristic of [(MGD)$_2$/Fe-$^{15}$NO], superimposed with the three-line spectrum characteristic of [(MGD)$_2$/Fe-$^{14}$NO], were observed in the liver and kidneys (see FIG. 4A and 4B, respectively). Again, the spectrum characteristic of the [(MGD)$_2$/Fe-$^{14}$NO] complex was detected in the mouse liver when $^{15}$N-arginine was omitted from the injection fluid (see FIG. 4A, the dotted lines).

EXAMPLE 6

Detection of the [(MGD)$_2$/Fe-NO] complex in the urine of LPS-treated mice

The effects of NMMA on ex vivo 9.5-GHz EPR spectra of the [(MGD)$_2$/Fe-NO] complex in the urine of the LPS-treated mice were determined. Thus, at 6 h after LPS treatment, mice were injected with the [(MGD)$_2$/Fe] complex, with and without i.p. injection of NMMA (50 mg/kg). The mice were sacrificed at 2 h after injection of the [(MGD)$_2$/Fe] complex. The urine samples were collected and the EPR measurement was carried out at 22° C.

A strong three-line spectrum characteristic of the [(MGD)$_2$/Fe-NO] complex was detected in the urine sample obtained from the LPS-treated mouse injected with the [(MGD)$_2$/Fe] complex (see FIG. 5A). The concentration of the complex is estimated to be 35.1 μM at 8 h after LPS challenge; the [(MGD)$_2$/Fe] complex was injected at 6 h after LPS.

Injection of NMMA markedly reduces the signal intensity (FIG. 5B) as well as the amounts of the [(MGD)$_2$/Fe-NO] complex (Table 2), which is consistent with the notion that the ·NO trapped by the [(MGD)$_2$/Fe] complex injected in the LPS-treated mice is produced mainly by inducible ·NO synthase. Thus, inducible ·NO synthase activities in living animals may be reduced by treatment with ·NO trapping agents as described herein.

Figure 6A:
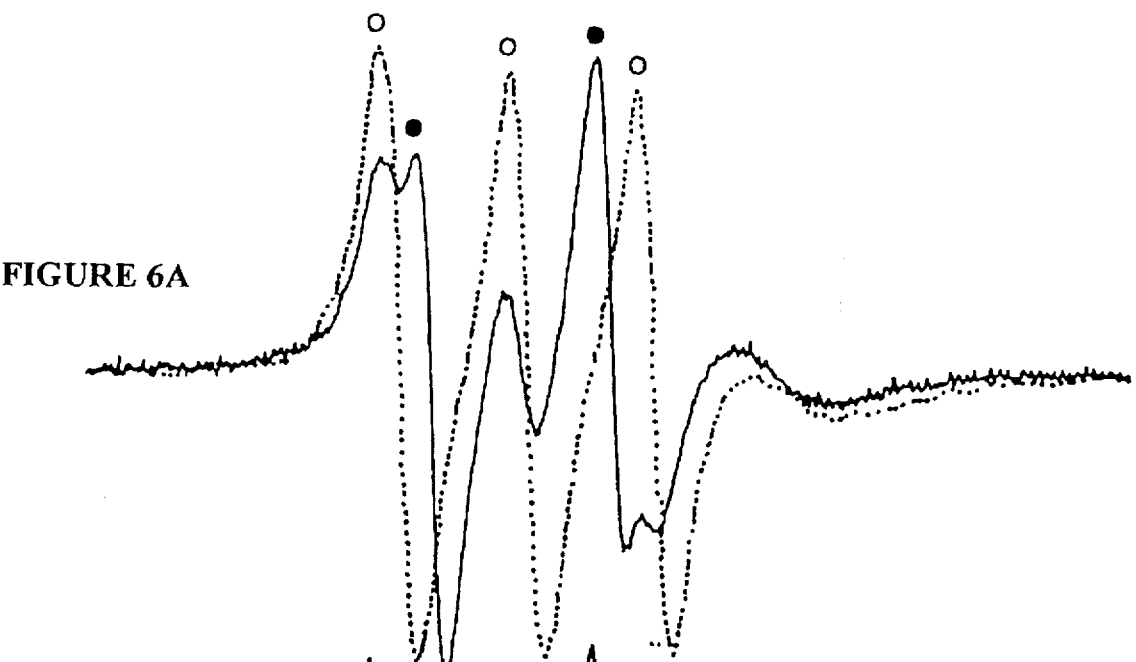
FIG. 6A presents spectra from the experiment wherein 10 mg of $^{15}$N-arginine were employed. The solid lines in FIG. 3A show a composite of two spectra, i.e., the two-line spectrum of the [(MGD)$_2$/Fe-$^{15}$NO] complex (●) and the three-line spectrum of the [(MGD)$_2$/Fe-$^{14}$NO] complex (○). The dotted three-line spectrum of the [(MGD)$_2$/Fe-$^{14}$NO] complex was obtained when $^{15}$N-arginine was omitted from the injection solutions.
Figure 6B:
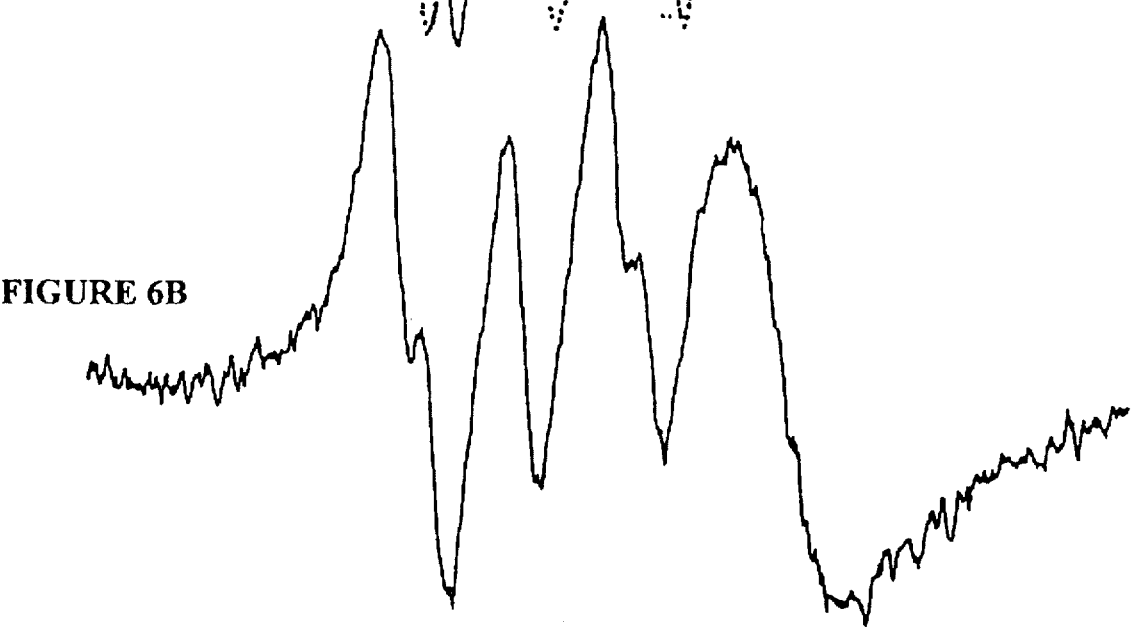
FIG. 6B presents spectra from the experiment wherein 5 mg of $^{15}$N-arginine were employed. Note: The signal intensity of the [(MGD)$_2$/Fe-$^{15}$NO] complex (○) decreased by at least one-half compared to that of the [(MGD)$_2$/Fe-$^{14}$NO] complex (○).

Furthermore, simultaneous injection of $^{15}$N-arginine (10 mg/mouse) and the [(MGD)$_2$/Fe] complex into the LPS-treated mice gave rise to a composite EPR spectrum, consisting of a two-line spectrum of the [(MGD)$_2$/Fe-$^{15}$NO] complex (closed circles), and a three-line spectrum of the [(MGD)$_2$/Fe-$^{14}$NO] complex (open circles) as shown in FIG. 6A (the solid lines). The pure three-line spectrum of the [(MGD)$_2$/Fe-$^{14}$NO] complex as depicted by the dotted lines in FIG. 6A was obtained when $^{15}$N-arginine was omitted from the injection solution. In addition, when $^{15}$N-arginine was administered at a level of 5 mg/mouse, the signal intensity of the [(MGD)$_2$/Fe-$^{15}$NO] complex was reduced compared to that of the [(MGD)$_2$/Fe-$^{14}$NO] complex (FIG. 6B). The results clearly confirm that the ·NO detected in the LPS-treated mouse urine was overproduced via the arginine-NO synthase pathway.

In summary, the isotopic tracer experiments using $^{15}$N-arginine have unambiguously demonstrated that the ·NO trapped by the [(MGD)$_2$/Fe] complex either in normal or the LPS-treated mice is produced via arginine-NO pathway (FIGS. 2, 3, 4 and 6). The authenticity of ·NO produced in vivo which is trapped by the [(MGD)$_2$/Fe] complex in our experimental systems is therefore firmly established.

The time-dependent increase in [(MGD)$_2$/Fe-NO] levels detected in urine samples after LPS administration is shown in Table 2.

TABLE 2

Time-dependent changes in the amounts of [(MGD)$_2$Fe—No] present in the LPS-treated mouse urine

| Conditions | [(MGD)$_2$Fe—NO], μM[a] |
|---|---|
| LPS-treated[b] | |
| 0 h | 1.4 ± 0.4(3)[c] |
| 2 h | 7.3 ± 2.2(3)* |
| 4 h | 18.2 ± 4.8(4)* |
| 6 h | 17.1 ± 4.8(4)* |
| 8 h | 35.1 ± 5.7(3)* |
| LPS-treated (after 6 h)[d] | |
| + NMMA (50 mg/kg) | 3.6 ± 0.9(4)† |
| + NMMA (100 mg/kg) | 3.8 ± 2.3(3)† |

[a]The amounts of [(MGD)$_2$Fe—NO] if mouse urine were determined as described in Table 1.
[b]At different times points after LPS challenge as indicated, the mice were injected subcutaneously with [(MGD)$_2$Fe], and were sacrificed 2 h later to collect urine for EPR measurement.
[c]The data presented are mean ± S.E. (number of mice).
[d]Various amounts on NMMA were injected intraperitoneally at 6 h after LPS challenge just prior to injection of [(MGD)$_2$Fe]. Urine was collected 2 h later.
*P < 0.05 compared with controls (see Table 1).
†P < 0.05 compared with the LPS-treated group at 6 h.

EXAMPLE 7

In Vivo Reduction of ·NO Levels by [(MGD)$_2$Fe] Complex in LPS-treated Mice

The time-dependent increase in plasma nitrate levels in LPS-treated mice was determined as previously described (see Komarov and Lai, supra). The results are summarized in Table 3.

TABLE 3

Effects of LPS and [(MGD)$_2$Fe] on total nitrate/nitrite levels in mouse plasma

| Conditions | Nitrate/Nitrite, μM[a] |
|---|---|
| Controls | 73 ± 7 (10)[d] |
| LPS-treated[b] | |
| 2 h | 103 ± 10 (6)* |
| 4 h | 291 ± 38 (6)* |
| 6 h | 506 ± 75 (4)* |
| 8 h | 638 ± 29 (8)* |
| LPS + [MGD)$_2$Fe] complex[c] | |
| 8 h | 336 ± 46 (3)*† |

[a]The nitrate/nitrite determination in the mouse plasma was performed as previously described (see Komarov and Lai, supra).
[b]The mice were sacrificed at different time points as indicated after intravenous injection of LPS.
[c]At 6 h after LPS challenge the mice were injected subcutaneously with [(MGD)$_2$Fe] and were sacrificed 2 h later.
[d]The data presented are mean ± S.E. (number of mice).
*P < 0.05 compared with controls
†P < 0.05 compared with the LPS-treated group at 8 h.

Nitrate levels are seen to increase with time after LPS challenge. Injection of the ·NO trapping agent, [(MGD)$_2$/Fe], reduced the nitrate level in the plasma by about one-half, a result suggesting that the trapping of ·NO by [(MGD)$_2$/Fe] in the LPS-treated mice prevents it from interaction with hemoglobin in the red blood cells, thereby reducing nitrate levels in the plasma. These results demonstrate that the administration of a dithiocarbamate-containing nitric oxide scavenger, such as the [(MGD)$_2$/Fe] complex, is effective to reduce in vivo ·NO levels in LPS-treated mice.

EXAMPLE 8

Although the route by which the subcutaneously injected spin-trapping reagent enters the tissues before its excretion into the urine is not yet known, it can be speculated that upon subcutaneous injection, the [(MGD)$_2$/Fe] complex diffuses across the capillary bed, where it interacts with ·NO produced by ·NO synthases to form the [(MGD)$_2$/Fe-NO] complex. The latter complex then enters the blood circulation and is eventually excreted and concentrated in the urine, thereby reducing in vivo ·NO levels. The isolated urine containing the [(MGD)$_2$/Fe-NO] complex was found to be stable at 4° C. for several hours. When the [(MGD)$_2$/Fe] complex was injected intravenously into normal or LPS-treated mice, the EPR signal of the [(MGD)$_2$/Fe-NO] complex was also detected in the urine. This suggests that regardless of the route of administration employed, dithiocarbamate-containing nitric oxide scavengers, such as the [(MGD)$_2$/Fe] complex, are capable of interacting with the ·NO produced in vivo to form a dithiocarbamate-Fe-NO complex, which reduces in vivo ·NO levels.

While the invention has been described in detail with reference to certain preferred embodiments thereof, it will be understood that modifications and variations are within the spirit and scope of that which is described and claimed.

That which is claimed is:

1. A method for the in vivo reduction of nitric oxide levels in a subject, said method comprising:
   administering to said subject an effective amount of at least one dithiocarbamate-containing nitric oxide scavenger.

2. A method for treating nitric oxide overproduction in a subject, said method comprising:
   administering to said subject an effective amount of at least one dithiocarbamate-containing nitric oxide scavenger.

3. A method according to claim 2 wherein said nitric oxide overproduction is associated with septic shock, ischemia, administration of cytokines, overexpression of cytokines, ulcer, ulcerative colitis, diabetes, arthritis, asthma, Alzheimer's disease, Parkinson's disease, multiple sclerosis, cirrhosis, allograft rejection, encephalomyelitis, meningitis, pancreatitis, peritonitis, vasculitis, lymphocytic choriomeningitis, glomerulonephritis, uveitis, ileitis, liver inflammation, renal inflammation, hemorrhagic shock, anaphylactic shock, burn, Crohn's disease or infection.

4. A method according to claim 2 wherein said nitric oxide overproduction is associated with septic shock, ischemia, administration of interleukin-1 (IL-1), administration of interleukin-2 (IL-2), administration of interleukin-6 (IL-6), administration of interleukin-12 (IL-12), administration of tumor necrosis factor (TNF), administration of interferon-gamma, ulcer, ulcerative colitis, diabetes, arthritis, asthma, Alzheimer's disease, Parkinson's disease, multiple sclerosis, cirrhosis or allograft rejection.

5. A method according to claim 2 wherein said nitric oxide overproduction is associated with septic shock.

6. A method according to claim 2 wherein said nitric oxide overproduction is associated with cytokine therapy.

7. A method according to claim 2 wherein said dithiocarbamate-containing nitric oxide scavenger comprises a physiologically compatible di- or tri-valent transition metal ion and a dithiocarbamate moiety having the structure:

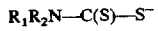

wherein:
$R_1$ is selected from a $C_1$ up to $C_{12}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl, substituted arylalkyl, or $R_1$ and $R_2$ can cooperate to form a 5-, 6- or 7-membered ring including N, R, and $R_2$, and $R_2$ is selected from a $C_1$ up to $C_6$ alkyl or substituted alkyl, or $R_2$ can cooperate with $R_1$, to form a 5-, 6- or 7-membered ring including N, $R_2$ and $R_1$.

8. A method according to claim 7 wherein said physiologically compatible di- or tri-valent transition metal is selected from iron, cobalt, copper or manganese.

9. A method according to claim 2 wherein said dithiocarbamate-containing nitric oxide scavenger is administered in combination with a cytokine, an antibiotic, a vasoactive agent, or mixtures thereof.

10. A method according to claim 9 wherein said cytokine is selected from interleukin-1 (IL-1), interleukin-2 (IL-2), interleukin-6 (IL-6), interleukin-12 (IL-12), tumor necrosis factor (TNF) or interferon-γ.

11. A method according to claim 9 wherein said vasoactive agent is selected from a catecholamine, noradrenaline, dopamine or dobutamine.

12. A method according to claim 2 wherein said dithiocarbamate-containing nitric oxide scavenger is delivered orally, intravenously, subcutaneously, parenterally, rectally or by inhalation.

13. A method according to claim 2 wherein said dithiocarbamate-containing nitric oxide scavenger is delivered in the form of a solid, solution, emulsion, dispersion, micelle or liposome.

14. A composition comprising a compound having the structure I and a pharmaceutically acceptable carrier therefor, wherein said pharmaceutically acceptable carrier is a sterile injectable solution or suspension, an organic or inorganic carrier suitable for enteral or parenteral administration, a non-toxic carrier for tablets, troches, lozenges, pellets, capsules, suppositories, emulsions, aqueous or oily suspensions dispersible powders or granules, liposomes, hard or soft capsules, syrups or elixirs, and wherein structure I is:

$$R_1R_2N-C(S)-S^-M^+ \quad (I)$$

wherein:

$R_1$ is selected from a $C_1$ up to $C_{12}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl, substituted arylalkyl or $R_1$ and $R_2$ can cooperate to form a 5-, 6- or 7-membered ring including N, R, and $R_2$, and $R_2$ is selected from a $C_1$ up to $C_6$ alkyl or substituted alkyl, or $R_2$ can cooperate with $R_1$ to form a 5-, 6- or 7-membered ring including N, $R_2$ and $R_1$, and M is a monovalent cation, provided, however, that the following compounds are excluded from the definition of Formula I, i.e., when $R_1$ is ethyl, $R_2$ is not ethyl; or when $R_1$ is $CH_2(CHOH)_4CH_2OH$, $R_2$ is not methyl, isoamyl, benzyl, 4-methylbenzyl or p-isopropylbenzyl; or when $R_1$ is $CH_2CO_2^-$, $R_2$ is not $CH_2CO_2$; or when $R_1$ is $CO_2^-$, $R_2$ is not $CH_3$; or when $R_1$ is $CH_2CH_2-OH$, $R_2$ is not $CH_2CH_2-OH$; or when $R_1$ and $R_2$ combined, together with the carbamate nitrogen, form a pyrrolidinyl-2-carboxylate.

15. A composition according to claim 14 wherein $M^+$ is selected from $H^+$, $Na^+$, $NH_4^+$ or tetraalkyl ammonium.

16. A composition comprising a compound having the structure II and a pharmaceutically acceptable carrier therefor, wherein said pharmaceutically acceptable carrier is a sterile injectable solution or suspension, an organic or inorganic carrier suitable for enteral or parenteral administration a non-toxic carrier for tablets, troches, lozenges, pellets, capsules, suppositories, emulsions, aqueous or oily suspensions, dispersible powders or granules, liposomes, hard or soft capsules, syrups or elixirs, and wherein structure II is:

$$[R_1R_2N-C(S)-S^-]_2M^{+2,+3} \quad (II)$$

wherein:

$R_1$ is selected from a $C_1$ up to $C_{12}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl substituted arylalkyl, or $R_1$ and $R_2$ can cooperate to form a 5-, 6- or 7-membered ring including N, R, and $R_2$, $R_2$ is selected from a $C_1$ up to $C_6$ alkyl or substituted alkyl, or $R_2$ can cooperate with $R_1$, to form a 5-, 6- or 7-membered ring including N, $R_2$ and $R_1$, and M is a physiologically compatible divalent or trivalent transition metal cation, provided, however, that the following compounds are excluded from the definition of Formula II, i.e., when $R_1$ is ethyl, $R_2$ is not ethyl; or when $R_1$ is $CH_2(CHOH)_4CH_2OH$, $R_2$ is not methyl, isoamyl, benzyl, 4-methylbenzyl or p-isopropylbenzyl; or when $R_1$ is $CH_2CO_2^-$, $R_2$ is not $CH_2CO_2^-$; or when $R_1$ is $CO_2^-$, $R_2$ is not $CH_3$; or when $R_1$ is $CH_2CH_2-OH$, $R_2$ is not $CH_2CH_2-OH$; or when $R_1$ and $R_2$ combined, together with the carbamate nitrogen, form a pyrrolidinyl-2-carboxylate.

17. A composition according to claim 16 wherein M is selected from $Fe^{+2}$, $Fe^{+3}$, $Co^{+2}$, $Co^{+3}$, $Cu^{+2}$, $Mn^{+2}$ or $Mn^{+3}$.

18. A composition according to claim 16 wherein:

$R_1$=a $C_1$ up to $C_{12}$ alkyl, substituted alkyl, alkenyl, substituted alkenyl, alkynyl or substituted alkynyl, wherein said substituents are selected from carboxyl, —C(O)H, oxyacyl, phenol, phenoxy, pyridinyl, pyrrolidinyl, amino, amido, hydroxy, nitro or sulfuryl, $R_2$=a $C_1$ up to $C_4$ alkyl or substituted alkyl, and $M=Fe^{+2}$ or $Fe^{+3}$.

19. A composition according to claim 16 wherein:

$R_1$=a $C_2$ up to $C_8$ alkyl or substituted alkyl, wherein said substituents are selected from carboxyl, acetyl, pyridinyl, pyrrolidinyl, amino, amido, hydroxy or nitro, $R_2$=methyl, ethyl, propyl or butyl, and $M=Fe^{+2}$.

20. A composition according to claim 16 wherein:

$R_1$=a $C_2$ up to $C_8$ alkyl or substituted alkyl, wherein said substituents are selected from carboxyl, acetyl, amido or hydroxy, $R_2$=methyl, ethyl, propyl or butyl, and $M=Fe^{+2}$.

21. A composition according to claim 14 wherein said pharmaceutically acceptable carrier is selected from a solid, emulsion, dispersion, micelle or liposome.

22. A composition according to claim 14 wherein said composition further comprises an enteric coating.

23. A composition comprising a compound having structure I in combination with a pharmacologically active agent, wherein structure I is:

$$R_1R_2N\text{—}C(S)\text{—}S^-M^+ \qquad (I)$$

wherein:

$R_1$ is selected from a $C_1$ up to $C_{12}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl, substituted arylalkyl or $R_1$ and $R_2$ can cooperate to form a 5-, 6- or 7-membered ring including N, R, and $R_2$, and $R_2$ is selected from a $C_1$ up to $C_6$ alkyl or substituted alkyl or $R_2$ can cooperate with $R_1$ to form a 5-, 6- or 7-membered ring including N, $R_2$ and $R_1$, and M is a monovalent cation.

provided, however, that the following compounds are excluded from the definition of Formula I, i.e., when $R_1$ is ethyl, $R_2$ is not ethyl; or when $R_1$ is $CH_2(CHOH)_4CH_2OH$, $R_2$ is not methyl, isoamyl, benzyl, 4-methylbenzyl or p-isopropylbenzyl; or when $R_1$ is $CH_2CO_2^-$, $R_2$ is not $CH_2CO_2$; or when $R_1$ is $CO_2^-$, is not $CH_3$; or when $R_1$ is $CH_2CH_2\text{—}OH$, $R_2$ is not $CH_2CH_2\text{—}OH$; or when $R_1$ and $R_2$ combined, together with the carbamate nitrogen, form a pyrrolidinyl-2-carboxylate.

24. A composition according to claim 23 wherein said pharmacologically active agent is selected from a cytokine, an antibiotic, a vasoactive agent, or mixtures thereof.

25. A composition according to claim 14 wherein said pharmaceutically acceptable carrier is a sterile injectable suspension or solution.

26. A composition according to claim 14 wherein said pharmaceutically acceptable carrier is an organic or inorganic carrier suitable for enteral or parenteral administration.

27. A composition according to claim 14 wherein said pharmaceutically acceptable carrier is a non-toxic carrier for tablets, troches, lozenges, pellets, capsules, suppositories, emulsions, aqueous or oily suspensions, dispersible powders or granules, liposomes, hard or soft capsules, syrups or elixirs.

28. A composition according to claim 16 wherein said pharmaceutically acceptable carrier is selected from a solid, emulsion, dispersion, micelle or liposome.

29. A composition according to claim 16 wherein said composition further comprises an enteric coating.

30. A composition according to claim 16 wherein said pharmaceutically acceptable carrier is a sterile injectable solution or suspension.

31. A composition according to claim 16 wherein said pharmaceutically acceptable carrier is an organic or inorganic carrier suitable for enteral or parenteral administration.

32. A composition according to claim 16 wherein said pharmaceutically acceptable carrier is a non-toxic carrier for tablets, troches, lozenges, pellets, capsules, suppositories, emulsions, aqueous or oily suspensions, dispersible powders or granules, liposomes, hard or soft capsules, syrups or elixirs.

33. A composition comprising a compound having structure II in combination with a pharmacologically active agent, wherein structure II is:

$$[R_1R_2N\text{—}C(S)\text{—}S^-]_2M^{+2,+3} \qquad (II)$$

wherein:

$R_1$ is selected from a $C_1$ up to $C_{12}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl substituted arylalkyl, or $R_1$ and $R_2$ can cooperate to form a 5-, 6- or 7-membered ring including N, R, and $R_2$.

$R_2$ is selected from a $C_1$ up to $C_6$ alkyl or substituted alkyl, or $R_2$ can cooperate with $R_1$, to form a 5-, 6- or 7-membered ring including N, $R_2$ and $R_1$, and M is a physiologically compatible divalent or trivalent transition metal cation.

provided, however, that the following compounds are excluded from the definition of Formula II, i.e., when $R_1$ is ethyl, $R_2$ is not ethyl; or when $R_1$ is $CH_2(CHOH)_4CH_2OH$, $R_2$ is not methyl, isoamyl, benzyl, 4-methylbenzyl or p-isopropylbenzyl; or when $R_1$ is $CH_2CO_2^-$, $R_2$ is not $CH_2CO_2^-$; or when $R_1$ is $CO_2^-$, $R_2$ is not $CH_3$; or when $R_1$ is $CH_2CH_2\text{—}OH$, $R_2$ it not $CH_2CH_2\text{—}OH$; or when $R_1$ and $R_2$ combined, together with the carbamate nitrogen, form a pyrrolidinyl-2-carboxylate.

34. A composition according to claim 33 wherein said pharmacologically active agent is selected from a cytokine, an antibiotic, a vasoactive agent, or mixtures thereof.

35. A composition according to claim 33 wherein said pharmaceutically acceptable carrier is a sterile injectable solution or suspension.

36. A composition according to claim 33 wherein said pharmaceutically acceptable carrier is an organic or inorganic carrier suitable for enteral or parenteral administration.

37. A composition according to claim 33 wherein said pharmaceutically acceptable carrier is a non-toxic carrier for tablets, troches, lozenges, pellets, capsules, suppositories, emulsions, aqueous or oily suspensions, dispersible powders or granules, liposomes, hard or soft capsules, syrups or elixirs.

38. A composition according to claim 33 wherein said pharmaceutically acceptable carrier is selected from a solid, emulsion, dispersion, micelle or liposome.

39. A composition according to claim 33 wherein said composition further comprises an enteric coating.

\* \* \* \* \*